(12) United States Patent
Antonelli et al.

(10) Patent No.: US 11,234,869 B2
(45) Date of Patent: Feb. 1, 2022

(54) GUIDING DEVICE OF AN APPARATUS FOR PRODUCING SANITARY ARTICLES FOR APPLYING A THREAD, AND RELATIVE METHOD

(71) Applicant: Fameccanica.Data S.p.A., San Giovanni Teatino (IT)

(72) Inventors: Gabriele Biagio Antonelli, Poggio Santa Maria (IT); Oscar Centorame, Giulianova (IT)

(73) Assignee: Fameccanica.Data S.p.A.

( * ) Notice: Subject to any disclaimer, the term of this patent is extended or adjusted under 35 U.S.C. 154(b) by 249 days.

(21) Appl. No.: 16/434,244

(22) Filed: Jun. 7, 2019

(65) Prior Publication Data
US 2019/0374389 A1    Dec. 12, 2019

(30) Foreign Application Priority Data

Jun. 8, 2018 (IT) ...................... 102018000006021

(51) Int. Cl.
| *A61F 13/15* | (2006.01) |
| *B65H 54/28* | (2006.01) |
| *B32B 5/26* | (2006.01) |
| *B65H 57/16* | (2006.01) |
| *B65H 57/26* | (2006.01) |
| *B65G 54/02* | (2006.01) |
| *A61F 13/49* | (2006.01) |

(52) U.S. Cl.
CPC .. *A61F 13/15593* (2013.01); *A61F 13/15764* (2013.01); *B32B 5/26* (2013.01); *B65G 54/02* (2013.01); *B65H 54/2833* (2013.01); *B65H 57/16* (2013.01); *B65H 57/26* (2013.01); *A61F 13/49009* (2013.01); *B32B 2555/02* (2013.01)

(58) Field of Classification Search
None
See application file for complete search history.

(56) References Cited

U.S. PATENT DOCUMENTS

| 4,801,345 A | 1/1989 | Dussaud et al. |
| 5,525,175 A | 6/1996 | Blenke et al. |

FOREIGN PATENT DOCUMENTS

| DE | 102013225653 A1 | 6/2015 |
| EP | 1148016 A2 | 10/2001 |
| WO | 0024663 A1 | 5/2000 |
| WO | 03002443 A1 | 1/2003 |

OTHER PUBLICATIONS

Italian Search Report dated Feb. 21, 2019. 7 pages.

*Primary Examiner* — Barbara J Musser
(74) *Attorney, Agent, or Firm* — RMCK Law Group PLC (57) ABSTRACT

A guiding device of an apparatus for producing sanitary articles for applying at least one thread onto a substrate intended for producing these sanitary articles, in which said guiding device is able to guide the thread quickly, accurately, and stably without being subject to wear and contamination problems, while ensuring reduced energy consumption. The present invention also relates to a method for applying a thread onto a substrate intended to produce sanitary articles.

7 Claims, 3 Drawing Sheets fig.1 fig.2a fig.2b fig.3 fig.4 fig.5

GUIDING DEVICE OF AN APPARATUS FOR PRODUCING SANITARY ARTICLES FOR APPLYING A THREAD, AND RELATIVE METHOD

CROSS-REFERENCE TO RELATED APPLICATION

This application claims priority to Italian Patent Application No. 102018000006021 filed Jun. 8, 2018. The disclosure of the above application is incorporated herein by reference in its entirety.

FIELD OF APPLICATION

Embodiments of the present invention relate to a guiding device of an apparatus for producing sanitary articles for applying a thread onto a substrate intended for producing these sanitary articles such as, for example, diapers, pull-ups, incontinence pads, sanitary napkins, or other articles designed to absorb body fluids.

Embodiments of the present invention relate to a guiding device of an apparatus for producing sanitary articles configured to apply elastic threads onto a substrate such as, for example, a continuous web material, a continuous composite sheet, or a discrete component.

Embodiments of the present invention also relate to a method utilizing one or more guiding devices of an apparatus for producing sanitary articles for applying threads onto a substrate intended for producing sanitary articles.

STATE OF THE ART

There are sanitary articles made with non-elastic materials which, in relation to the specific articles to be made and to the desired wearability to be achieved, can be rendered elastic, for example, by trapping elastic threads between them.

A typical example of applying elastic threads in a diaper is that of the waist band, or of the containment barriers of the legs, in which pleated regions are made by means of these elastic threads that provide a certain extensibility to the material.

Entrapment of pre-tensioned elastic threads between two sheets of non-elastic materials, for example, a non-woven fabric is known by locally fixing the sheets together and/or the elastic threads tensioned to the sheets so as to locally constrain the elastic threads along a pattern of entrapment.

In relation to the specific entrapment pattern and the elastic action to be provided to the specific area of the article, the elastic thread is guided along a specific path adjusting the feeding speed during its application on the substrate.

Some guiding devices comprise a linear guide defining a linear direction and a carriage provided with a thread-carrying tool which is configured to move on the linear guide in relation to the specific entrapment pattern to be achieved.

During the movement of the carriage on the linear guide, the carriage makes multiple changes of direction that significantly wear out both the wheels, or balls, of the carriage, and the surface of the linear guide, requiring frequent maintenance and/or lubrication.

Due to the wear of the balls of the carriage and the surface of the linear guide, the thread is typically supplied to the substrate incorrectly, making the resulting sanitary articles non-conformant to the required specifications.

The Applicant has experimented and developed solutions which envisage the use of aerostatic shoes that generate an air cushion defining a gap between the carriage and the linear guide. Although these solutions have advantages over contamination and related problems, they are, however, expensive from an energy point of view, and require a dedicated air supply and management system.

The need to provide a solution capable of overcoming the problems relating to wear and which—at the same time—allows overcoming the problems connected with the use of aerostatic shoes has materialized.

Known solutions have been developed in sectors that are significantly different from that of the present invention which, as they have been studied and for the performances they are able to achieve, cannot be used in an apparatus for making sanitary articles.

The document EP-A-1.148.016 (EP'016) describes an apparatus for winding a thread onto a reel, in which the apparatus consists of a carriage movable on a magnetic guide and is configured to reach speeds from 2 m/s to 6 m/s.

The document EP'016 describes and addresses the problem of changing direction of the movable carriage and in particular proposes the use of a control unit configured for controlling the speed of the movable carriage during the inversion.

It is known that the reel-winding systems present problems mainly related to the winding in succession of the turns which, if incorrectly overlapped, can make the reel non-homogeneous.

The apparatuses for winding thread on reels envisage that the movable carriage can perform repeated movements along a linear direction between two fixed and spaced-apart end positions of a limited length.

In the field of apparatuses for producing sanitary articles, it is known that the thread-guiding devices must convey the threads so as to produce various and different entrapment patterns quickly so as to produce different formats of sanitary articles.

In the field of sanitary articles, it is required that the movable carriage is moved with a linear stroke even greater than 30 cm and with speeds and accelerations equal to if not greater than those of the field of apparatuses for producing reels.

The document DE-A-10.2013.225653 (DE'653) describes an apparatus for winding a thread onto a reel consisting of a movable carriage coupled to a magnetic beam.

The movable carriage is kept spaced apart from the magnetic beam by means of a permanent magnetic field obtained by the interaction between a plurality of permanent magnets arranged on the movable carriage and the magnetic beam itself.

This known solution envisages that the movable carriage can move passively along the longitudinal extension in relation to the position of the thread.

The apparatus described in DE'653 also comprises aerostatic brakes placed at the ends of the magnetic beam and oriented towards the movable carriage. These aerostatic brakes are configured to slow down the movable carriage when the latter reaches the ends so that it does not hit against the carriage.

DE'653 also describes the possibility of using aerostatic brakes as a means of moving the movable carriage that, under the thrusting action of compressed air jets from the aerostatic brakes, can move along the magnetic beam.

This known solution presents considerable problems in that it is not possible to precisely control the movable carriage and, moreover, it is not possible to move the movable carriage so as to obtain varied and different entrapment patterns of the threads between the sheets with the speeds required in the field of sanitary articles.

The document WO-A-00/24663 (WO'663) describes a system for conveying a thread towards a reel provided with a rotating element configured to feed the thread rotating about an axis of rotation defined by a pin to which it is connected.

The rotating element of WO'663 is positioned spaced apart from a plane and is moved by means of a magnetic movement assembly. The rotating element is provided with an inductive circuit which, when powered, couples with the magnetic field generated by magnets installed on the plane.

In addition to the problems of the prior art already described, this known solution has the further problem that the end that guides the thread towards the reel follows a curvilinear path, and even if the rotating element is spaced apart from the plane it can bend towards the latter in relation to the direction of the thread and its elasticity.

Furthermore, this last known solution cannot be used in an apparatus for producing sanitary articles since the performances required in the field cannot be satisfied by it.

The problems that an expert in the field of apparatuses for producing sanitary articles must confront, and in particular those relating to the high speed of movement of the thread guide, as well as those relating to the possibility of producing varied and different patterns of entrapment of the threads between two sheets, are neither described nor addressed by known solutions.

The known solutions cannot be used in apparatuses for producing sanitary articles that require speeds of up to 10 m/s with accelerations at full speed even higher than 230 m/s$^2$ and with strokes even greater than 30 cm.

These known solutions do not allow sanitary articles to be produced that have sheets between which elastic threads are trapped quickly and with the desired pattern of entrapment of the threads between the sheets, in which the positioning error of the thread along the desired entrapment pattern does not exceed 5 mm.

There is therefore a need to improve and make a guiding device available of an apparatus for producing sanitary articles to apply threads onto a substrate intended for producing these sanitary articles, which overcomes at least one of the drawbacks of the prior art.

One object of the present invention is to provide a guiding device capable of overcoming the problems related to wear, which does not require frequent maintenance and lubrication, and which—at the same time—allows the thread to be supplied on the substrate in a reproducible and precise manner.

Another object of the present invention is to provide a guiding device capable of supplying the thread in a stable, controlled and high-speed manner.

Another object of the present invention is to provide a guiding device capable of overcoming the problems relating to aerostatic shoes, and which—at the same time—allows reduction of energy consumption and overcome problems relating to wear.

It is a further object of the present invention to provide a method using one or more guiding devices for applying threads onto a substrate intended for producing sanitary articles that is able to overcome at least one of the problems of the prior art.

The present Applicant has devised, tested and embodied this invention to overcome the shortcomings of the prior art and to obtain these and additional objects and advantages.

SUMMARY OF THE INVENTION

The present invention is expressed and characterized in the independent claims, while the dependent claims set out other characteristics of the present invention or variants of the idea of the main solution.

In accordance with the aforesaid objects, the present invention relates to a guiding device of an apparatus for producing sanitary articles for applying at least one thread onto a substrate intended to produce these sanitary articles which comprises a first body movable along a linear direction and configured to guide the thread, and at least one second body fixed with respect to the first body. For example, the substrate may comprise a continuous web or other material.

In accordance with an aspect of the present invention, the guiding device comprises a spacer assembly configured to space the first body apart from the at least one second body by means of a magnetic force, and a magnetic movement assembly associated with the first body and with said at least one second body to move the first body along the linear direction by another magnetic force.

The spacer assembly comprises at least one air dispenser configured to deliver air so as to hinder the access and/or deposition of contaminants between the first body and the at least one second body.

Thanks to the action of the spacer assembly, a gap is formed between the first body and the at least one second body, also considering any elements associated with them.

Thanks to the presence of the spacer assembly it is not necessary to use aerostatic shoes and, therefore, there is a considerable energy saving, since dedicated air supply and management systems are not required.

This solution also has the advantage of being compact and silent with respect to other solutions that use aerostatic shoes, since it does not envisage the presence of compressors and/or air filters, nor does it provide any air supply during use.

Thanks to the possibility of generating two dedicated magnetic fields, respectively, for distancing the bodies and for reciprocally moving them, allows simplifying the system, making positioning and movement precise, stable and reproducible.

According to possible embodiments, the spacer assembly may comprise a plurality of magnetic spacer elements each configured to generate a respective magnetic force in order to locally distance the first body from the at least one second body.

In accordance with possible embodiments, the magnetic spacer elements can be placed at the sides of the magnetic movement assembly so that the magnetic fields generated by the magnetic spacer elements do not hinder the action of the magnetic field generated by the magnetic movement assembly.

According to possible embodiments, the spacer assembly may comprise at least one air dispenser configured to deliver air so as to hinder access and/or deposition of contaminants in the gap.

According to possible embodiments, the magnetic drive assembly may comprise a plurality of magnets and means for generating a variable magnetic field in order to cooperate, in use, with at least part of the magnets to move the first body along the linear direction.

According to possible embodiments, the plurality of magnets can be placed on the first body and the means for generating a variable magnetic field can be placed on the at least one second body.

In accordance with possible embodiments, the guiding device may comprise at least two second bodies between which the first body is interposed.

According to possible embodiments, the ratio between the respective lengths along the linear direction of the first body and of the second body can be greater than 1.

In agreement with possible embodiments, the guiding device may comprise a support member connected to the first body and configured to connect a tool to carry the thread, in which the support member extends, at least in part, out of the at least one second body.

In accordance with possible embodiments, the present invention also relates to a method for applying a thread onto a substrate intended to produce sanitary articles.

In accordance with one aspect of the present invention, the method envisages: associating the thread with a first body movable along a linear direction; spacing the first body apart from the at least one second body, fixed with respect to the first body by means of a magnetic force; and moving the first body along the linear direction by a magnetic force so as to guide the thread to apply it on the substrate.

According to possible embodiments, the method may envisage supplying air by means of an air dispenser so as to hinder access and/or deposition of contaminants between the first body and the at least one second body, wherein the air dispenser is included in the spacer assembly.

ILLUSTRATION OF THE DRAWINGS

These and other characteristics of the present invention will become clear from the following description of embodiments, given as a non-limiting example, with reference to the attached drawings wherein.

To facilitate understanding, identical reference numbers have been used, where possible, to identify identical common elements in the Figures. It should be understood that elements and characteristics of an embodiment can be conveniently incorporated in other embodiments without further specification.

DESCRIPTION OF THE EMBODIMENTS

Embodiments described herein, with reference to the figures, refer to a guiding device 10 of an apparatus for producing sanitary articles for applying at least one thread 11 onto a substrate 12 intended to produce these sanitary articles.

By way of non-limiting example, reference will be made hereinafter to a single elastic thread 11 and to a substrate 12 that comprises at least one non-woven fabric material.

The substrate 12 can be a continuous web, a discrete element, or another component of a sanitary article. For example, the guiding device 10 allows application of an elastic thread 11 between two substrates 12 of flexible but not elastic fabric, and entrapment between them so as to make the composite fabric elastic.

According to possible embodiments, the guiding device 10 comprises a first body 13 movable along a linear direction X and configured to guide the thread 11, and at least one second body 14 fixed with respect to the first body 13.

According to possible embodiments, the first body 13 is configured to carry a thread 11 that is supplied thereto, which is guided towards the substrate 12 by moving the first body 13 itself.

In accordance with an aspect of the present invention, the guiding device 10 comprises a spacer assembly 16 configured to space the first body 13 apart from the at least one second body 14 by means of a magnetic force, and a magnetic movement assembly 15 associated with the first body 13 and with said at least one second body 14 for moving the first body 13 along the linear direction X by means of another magnetic force. The other magnetic force can be generated through a respective variable magnetic field.

According to possible embodiments, thanks to the action of the spacer assembly 16, a gap 17 is formed between the first body 13 and the at least one second body 14, also considering any elements associated with them.

As will be clear below and as can be seen in the drawings, for example, the possible elements associated with the first body 13 and/or the at least one second body 14 may comprise the magnets 18, the means 19 for generating a variable magnetic field, the magnetic spacer elements 31, 131, or other elements.

According to possible embodiments, the minimum width of the gap 17 can be between 1 μm and 20 μm. According to possible embodiments, the minimum width of the gap 17 can be between 5 μm and 15 μm.

According to possible embodiments, the magnetic drive assembly 15 may comprise a plurality of magnets 18 and means 19 for generating a variable magnetic field in order to cooperate, in use, with at least part of the magnets 18 to move the first body 13 along the linear direction X.

This embodiment makes it possible to control the movement of the first body 13 through the means 19 for generating a variable magnetic field without the need to also intervene directly on the magnets 18, whether the magnets are configured to generate a variable magnetic field, or if they are electromagnets.

This greatly simplifies the operations of control and maintenance on the components and basically limits any spare parts to just the means 19 for generating a variable magnetic field.

According to possible embodiments, the magnetic movement assembly may comprise a plurality of magnets 18, placed on the first body 13, and means 19 for generating a variable magnetic field, placed on the at least one second body 14.

According to possible embodiments, the guiding device 10 may comprise at least one management and control unit 33 configured to modulate the variable magnetic field generated by the means 19, by means of a control signal sent by said management and control unit 33 to the means 19.

Thanks to the management and control unit 33 it is possible to make the guiding device 10 flexible, in other words able to move the first body 13 in accordance with the specific production requirements. This allows entrapment patterns of the threads 11 to be created in the substrates 12 and therefore enables production of various and different types of sanitary articles.

By modulating the variable magnetic field in the desired manner, the first body 13 performs various movements in relation to the sanitary article to be produced.

Thanks to this aspect, it is no longer necessary to completely replace the guiding device 10 for each type of sanitary article to be made.

Moreover, the possibility of also being able to modify the movement of the first body 13 during feeding of the thread 11 makes it possible to manage the pull of the thread in relation to the elasticity of the thread 11 and to the instantaneous position of the first body 13 along the linear direction X.

According to possible embodiments, modulating the variable magnetic field to modify—in real time—the movement of the first body 13 to compensate for the pulling effects of the thread 11 can be determined once the linear direction X has been defined with respect to the application point of the thread 11 on the substrate 12.

In accordance with possible embodiments, the magnets 18 can be permanent magnets, such as, for example, magnets comprising iron, or other magnetic elements. For example, the magnets 18 may comprise neodymium, iron and boron which, when combined, exhibit high energy densities and operating temperatures.

According to possible embodiments, the means 19 for generating a variable magnetic field may comprise one or more reels possibly coupled to ferromagnetic cores, which allow generation of a variable magnetic field in relation to the electric current that is supplied to them.

These reels can be spatially positioned so as to generate—each time—a magnetic field having the desired distribution of intensity and direction.

According to possible embodiments, the means 19 for generating a variable magnetic field can be magnetic actuators.

In relation to the specifications of the variable magnetic field generated by the means 19 and to the mutual position of the magnets 18 with respect to the means, the first body 13 is moved along the linear direction X.

According to possible embodiments, the plurality of magnets 18 can be placed on the first body 13, and the means 19 for generating a variable magnetic field can be placed on the at least one second body 14.

This aspect makes it possible to position the means 19 that require a connection towards power supply sources on the at least one second fixed body 14, while the magnets 18 that do not require connections to further elements are positioned on the first movable body 13.

This makes it possible to make the movable body 13 light and devoid of additional bulky or obstructing elements, such as for example the connections to the power supply sources, which make assembly and use complex.

According to possible embodiments, the magnets 18 can be placed in succession along the extension of the first body 13 which extends along the linear direction X.

In accordance with possible embodiments, the means 19 for generating a variable magnetic field can be placed on the at least one second body 14 so that they face the plurality of magnets 18.

By positioning the means 19 for generating a variable magnetic field on the at least one fixed second body 14, it is possible to size and position the connections to the source of electrical power that supplies the means 19 so that they are stable and do not obstruct the movement of the first body 13. This aspect simplifies any maintenance operations on the guiding device 10.

According to possible embodiments, the first body 13 can be a profiled bar having an L-shaped cross-section defined by a long side 20 and a short side 21.

As will become clear later in the description, this conformation of the first body 13 allows the position of the first body to be stabilized with respect to that of the at least one second body 14 along both directions perpendicular with respect to the linear direction X.

In accordance with possible embodiments, the magnets 18 can be placed on the long side 20 of the profiled bar. For example, the magnets 18 can be placed in the central area of the long side 20 which extends along the linear direction X.

In this way, the short side 21 is not affected by the action of the means 19 on the magnets 18 and can advantageously be used to connect a thread-carrying tool, also referred to below as a support member 24.

In order to contain the temperature within the operating limits of the magnets 18 and of the means 19 without risk of damaging and/or deforming the first body 13, the at least one second body 14, or other, the guiding device 10 may comprise one or more insulating elements 22 associated with the magnets 18 and/or the means 19 for generating a variable magnetic field, so as to thermally insulate the first body 13 and the at least one second body 14 from the heat generated by the magnets 18 and/or by the means 19.

Figure 1:
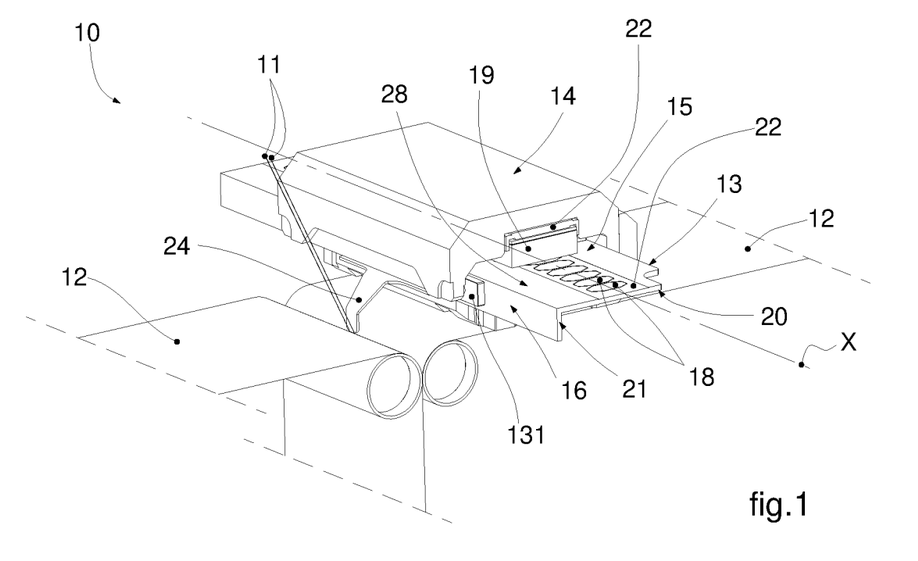
FIG. 1 is a perspective view of a guiding device of an apparatus for producing sanitary articles according to a possible embodiment of the present invention.
Figure 2A:
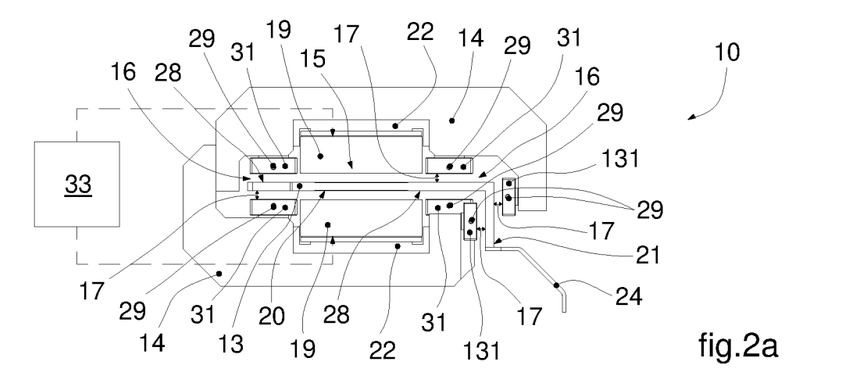
FIGS. 2a and 2b are two side views of two guiding devices of an apparatus for producing sanitary articles according to possible embodiments of the present invention.
Figure 2B:
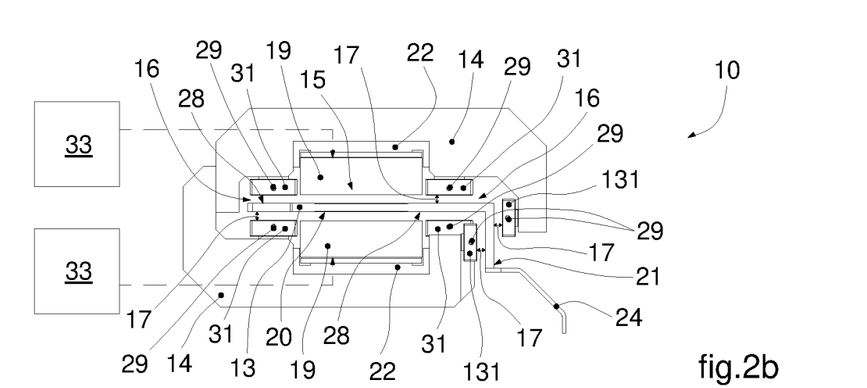
Figure 3:
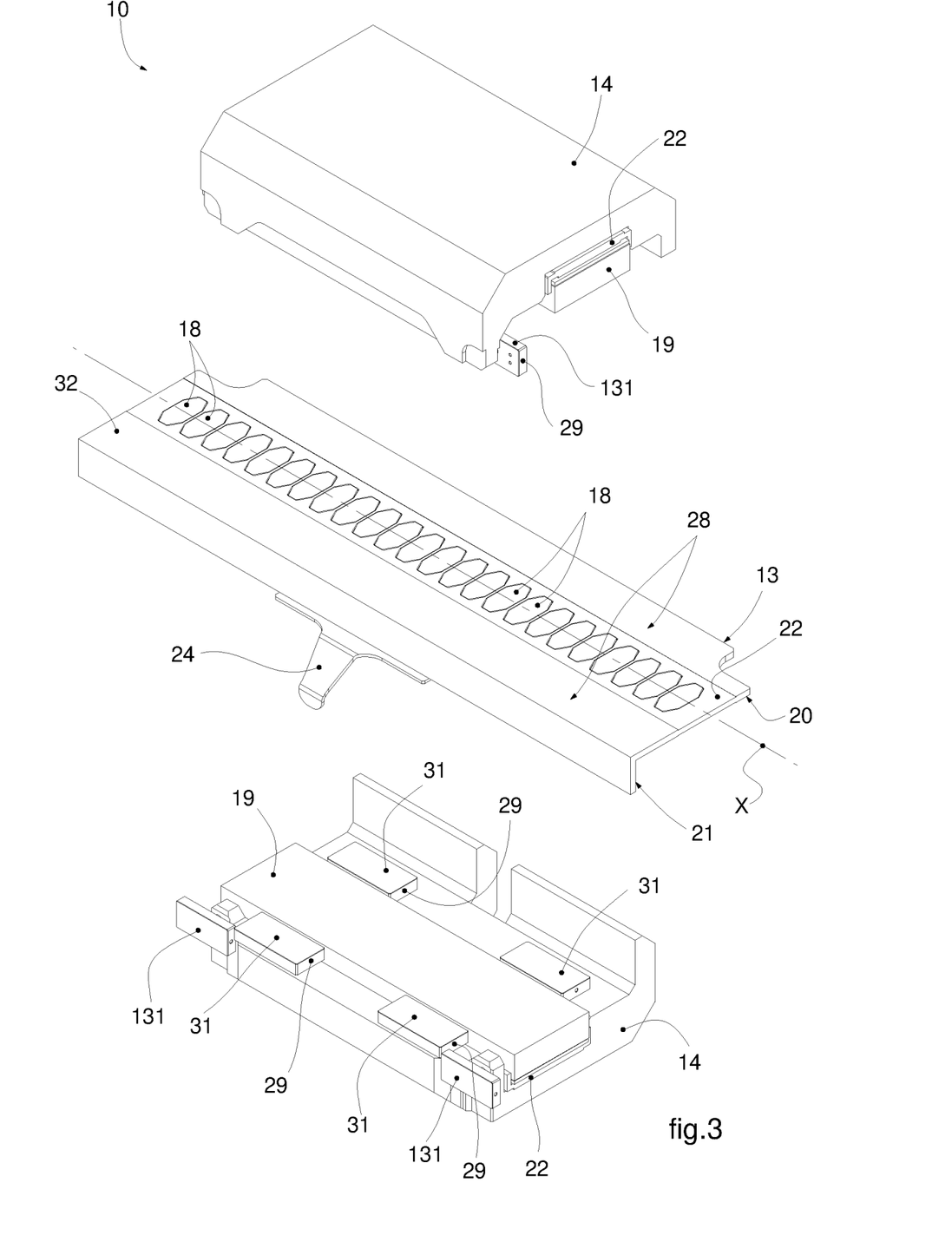
FIG. 3 is an exploded view of FIG. 1.
Figure 4:
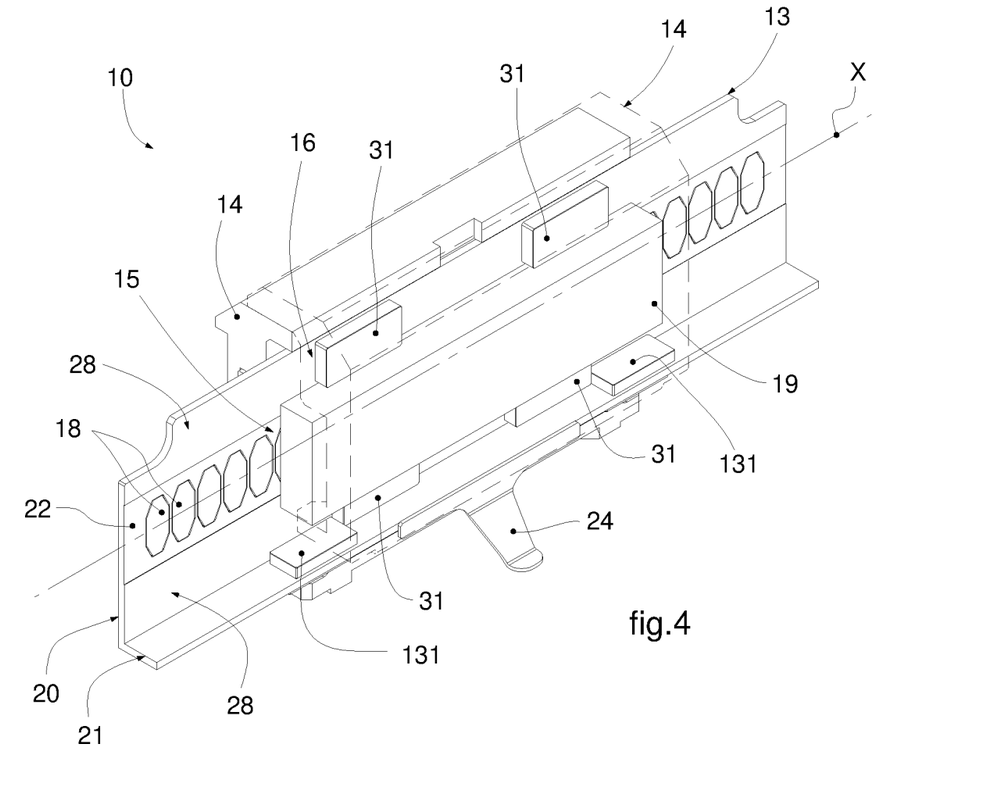
FIG. 4 is a schematic perspective view of a guiding device of an apparatus for producing sanitary articles according to a possible embodiment of the present invention.
Figure 5:
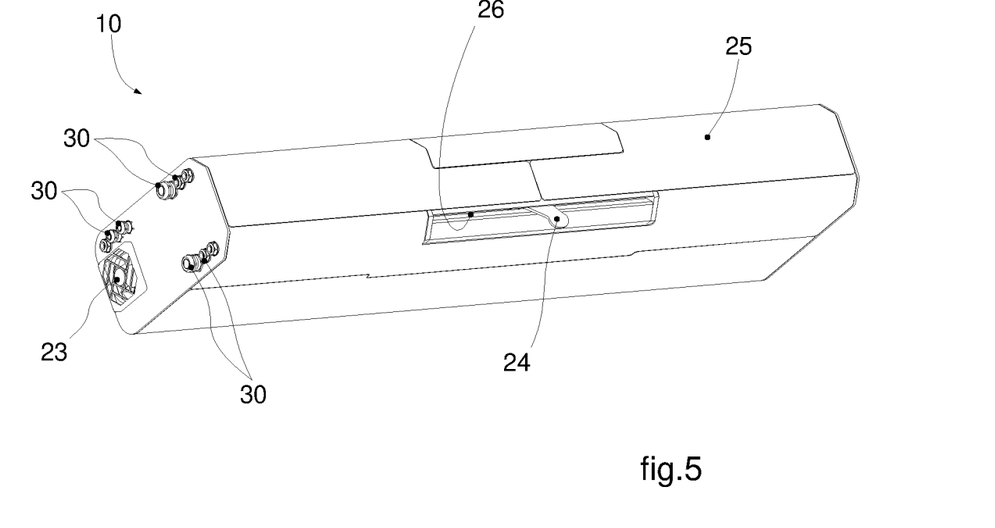
FIG. 5 is a perspective view of a guiding device of an apparatus for producing sanitary articles according to a possible embodiment of the present invention.

For example, the insulating elements 22 may comprise epoxy glass or other heat-insulating materials. With reference to FIG. 1, the insulating element 22 can be placed between the magnets 18 and the first body 13 along the linear direction X and/or also between the means 19 and the second body 14.

According to possible embodiments, the guiding device 10 may comprise a cooling unit 23 configured to cool at least the first body 13 by means of a cooling fluid.

According to possible embodiments, the guiding device 10 may comprise a cooling unit 23 configured to cool at least the second body 14 by means of a cooling fluid.

In accordance with possible embodiments, the cooling unit 23 may comprise cooling ducts integrated or coupled to the second body 14 and fluidly connected to a cooling source which supplies a cooling fluid.

Still with the aim of maintaining the temperature within the operating values and guaranteeing a constant air circulation, the cooling unit 23 may comprise one or more fans configured to circulate air along the linear direction X.

In accordance with possible embodiments, the fans are configured to generate an air flow that circulates along the linear direction X and exits through the opening from which the support member 24 protrudes.

This aspect hinders the access of contaminants inside the guiding device 10 and in particular in the gaps 17 between the first body 13 and the second body 14.

According to possible embodiments, the means 19 for generating a variable magnetic field can be coupled to a cooling unit 23 configured to cool the means 19 and/or the at least one second body 14 to bring and maintain the temperature within the operating values.

In accordance with possible embodiments, the guiding device 10 may comprise at least two second bodies 14 between which the first body 13 is interposed.

According to possible embodiments, each of the at least two second bodies 14 is provided with respective means 19 for generating a respective variable magnetic field.

This aspect is particularly advantageous in that the combined action of the two second bodies 14 between which the first body 13 is interposed provides greater stability and uniformity of thrust to the first body 13.

According to possible embodiments, the magnets 18 are placed on both sides of the long side 20 of the first body 13 along the linear direction X, while the means 19 are placed on the two second bodies 14 facing towards a respective face of the long side 20 of the first body 13.

The combined action of the means 19 for generating a magnetic field on the magnets 18 allows the first body 13 to be maintained in the correct position, significantly reducing the load supported by the spacer assembly 16.

This solution allows the movement of the first body 13 to be sped up even more and, furthermore, allows reduction of the load on the second bodies 14 considered individually with the same thrust obtained with a single second body 14 provided with means 19 for generating a variable magnetic field.

The guiding device 10 of an apparatus for producing sanitary articles according to the present invention can reach speeds of movement of the first body 13 of up to 12 m/s$^2$ with accelerations at full speed even higher than 230 m/s$^2$ and with strokes even greater than 30 cm.

The present invention has the considerable advantage that it allows generation of high energy which can be used to supply the guiding device 10 itself and/or other devices.

Unlike the prior art in which accelerations and decelerations can reach about 100-150 m/s$^2$, the combined and synergic action of the spacer assembly 16 and of the magnetic movement assembly 15 allow accelerations and decelerations of up to 250-350 m/s$^2$ to be reached.

The variations in reciprocal speed of the magnets 18 with respect to the means 19 and, in particular, the deceleration step allows generation of an electric current in the means 19 which can be conveyed towards the network and/or other components according to the specific requirements.

According to possible embodiments, the electrical energy generated during the deceleration step of the first body 13 on which the magnets 18 are arranged can be used to supply the spacer assembly 16 and/or the magnetic power supply assembly 15. This makes it possible to make the guiding device 10 at least partly self-powered.

According to possible embodiments, the ratio between the respective lengths along the linear direction X of the first body 13 and of the second body 14 can be greater than or equal to 1.

According to possible embodiments, the ratio between the respective lengths along the linear direction X of the first body 13 and of the second body 14 can be from 1 to 3.

According to possible embodiments, the ratio between the respective lengths along the linear direction X of the first body 13 and of the second body 14 can be from 1.5 to 2.5.

These geometric relationships between the first body 13 and the at least one second body 14 have been set up so as to balance and optimize the relationship between bulkiness and energy transfer efficiency.

These identified geometric ratios allow the totality of the magnetic field generated by the means 19 to be used for generating a variable magnetic field of the at least one second body 14 to move the first body 13.

In fact, it appears that the area of action of the means 19 on the at least one second body 14 faces, for its greater part, or for its totality, towards the area of the first body 13 where the magnets 18 are arranged.

This allows the first body 13 to be moved without high electromagnetic losses of the means 19 for generating a variable magnetic field, since the magnetic energy generated by these means is transferred to the first body 13.

In agreement with possible embodiments, the guiding device 10 may comprise a support member 24 connected to the first body 13 and configured to connect a tool to carry the thread 11, in which the support member extends, at least in part, out of the at least one second body 14.

This aspect makes it possible to position and guide the thread 11 in a region which is far from both the magnetic movement unit 15 and the spacer assembly 16. This is advantageous in that the thread 11, the tool and the support member 24 are not affected by the magnetic field or by the action of the spacer assembly 16.

According to possible embodiments, the support member 24 and/or the tool can simultaneously carry and guide a plurality of threads 11.

According to possible embodiments, the support member 24 can be fixed to the short side 21 of the first body 13 by means of suitable fastening elements, such as for example pegs, welding joints, or the like. According to possible embodiments, the support member 24 can be made in a single piece with the first body 13.

In accordance with possible embodiments, the guiding device 10 may comprise a casing 25 configured to contain the first body 13, the at least one second body 14, the spacer assembly 16 and the magnetic movement assembly 15.

In order to limit exposure to contamination and make the guiding device 10 safe for operators, the casing 25 is provided with a slot 26 along which at least part of the support member 24 comes out and slides.

According to possible embodiments, the casing 25 may comprise a plurality of shells which can be connected to each other in a removable manner.

In accordance with possible embodiments, the connectors 30 assigned to the electrical connection or to the fluidic connection, be it air, or with any other gas, as well as with a cooling fluid, can be arranged on the side faces of the casing 25 placed transversely with respect to the linear direction X.

According to possible embodiments, the spacer assembly 16 may comprise a plurality of magnetic spacer elements 31, 131 each configured to generate a respective magnetic field configured to produce a respective magnetic force in order to locally distance the first body 13 from the at least one second body 14.

This aspect allows distancing the first body 13 away from the at least one second body 14 in a desired manner and also when diversification is required, making the guiding device 10 flexible for use in multiple conditions and settings.

According to possible embodiments, the guiding device 10 may comprise a first body 13 and a single second body 14. For example, the first body 13 can be a profiled bar, or a profiled bar having an inverted-U-shaped cross-section.

According to possible embodiments, for each second body 14 of the guiding device 10, the spacer assembly 16 may comprise at least one magnetic spacer element 31, which acts to space the first body 13 apart from the respective second body 14 along a first direction perpendicular with respect to the linear direction X and at least one other magnetic spacer element 131, which acts to space the first body 13 away from the respective second body 14 along a second direction perpendicular to the linear direction X.

According to possible embodiments, the first and the second perpendicular directions are perpendicular to each other.

For example, if the first body 13 is a profiled bar having an L-shaped cross-section and there are two second bodies 14, the spacer assembly 16 may comprise at least one pair of magnetic spacer elements 31 configured to space apart the long side 20 from the two second bodies 14 along a first direction perpendicular to the surface 32 of the first body 13 affected by the magnetic movement assembly 15, or the surface 32 facing the means 19 for generating the variable magnetic field, or rather the surface 32 on which the magnets 18 are arranged.

According to possible embodiments, the spacer assembly 16 may comprise a pair of magnetic spacer elements 131 configured to space apart the short side 21 from the two second bodies 14 along a second direction perpendicular to the first perpendicular direction.

This aspect allows the first body 13 to be stabilized and kept at a distance from the second bodies 14 along both directions perpendicular to the linear direction X.

It is understood that the considerations relating to the illustrative case of a first body 13 comprised between two second bodies 14 can be extended to the case of a single second body 14 by suitably adapting geometries and/or reciprocal positions of the first body 13, of the second body 14, as well as of the elements possibly associated with them.

According to possible embodiments, the magnetic spacer elements 31, 131 may comprise magnets and/or means for generating a magnetic field and are located on the sides of the magnetic movement assembly 15.

In this way, the magnetic fields generated by the magnetic spacer elements 31, 131 do not hinder the action of the magnetic field generated by the magnetic movement assembly 15.

For example, the magnetic spacer elements 31, 131 can be substantially configured in a manner analogous to the magnetic movement assembly 15, but with the object of distancing the first body 13 from the at least one second body 14 instead of moving the first body 13 with respect to the at least one second body 14.

In accordance with possible embodiments, the magnetic spacer elements 31, 131 can be located either on the long side 20, or on the short side 21.

In accordance with possible embodiments, the magnetic spacer elements 31, 131 can be placed at the sides of the magnetic movement assembly 15 so that the magnetic fields generated by the magnetic spacer elements 31, 131 do not hinder the action of the magnetic field generated by the magnetic movement assembly 15.

According to possible embodiments, the magnetic spacer elements 31 can be facing towards the side portions 28 of the first body 13 between which the magnets 18 are arranged.

This aspect allows both stabilization of the positioning of the first body 13 with respect to the at least one second body 14, and separation of the area of action of the magnetic movement assembly 15 with respect to the areas of action of the magnetic spacer elements 31.

The presence of the magnetic spacer elements 31 on the at least one second body 14 on the sides of the magnetic movement assembly 15 allows positioning of the first body 13 on a stable and defined plane of arrangement, while ensuring continuity of operation without undesired interference between the spacer assembly 16 and the magnetic drive assembly 15.

According to possible embodiments, the side portions 28 can be provided with tracks comprising anti-friction material configured to reduce the friction between the first body 13 on the at least one second body 14 if there is contact between the first body and the second body. For example, the track may include a material called Turcite®, or other similar materials.

According to possible embodiments, the spacer assembly 16 may comprise at least one air dispenser 29 configured to deliver air so as to hinder access and/or deposition of contaminants in the gap 17.

In accordance with possible embodiments, one or more air dispensers 29 can be placed between the magnetic spacer elements 31, 131, or integrated in these elements.

This aspect allows the contaminants to be removed from the gap 17 by means of suitable air dispensers. For example, during use of the magnetic movement assembly 15 it is possible to operate the air dispenser continuously, intermittently, or as needed. Moreover, the air dispensers 29 can also be used to cool the magnetic movement assembly 15.

In accordance with possible embodiments, the present invention also relates to a method using a guiding device 10 of an apparatus for producing sanitary articles as described in any one of the embodiments described for applying a thread 11 onto a substrate 12 intended for producing sanitary articles.

In accordance with one aspect of the present invention, the method envisages: associating the thread 11 with a first body 13 movable along a linear direction X; spacing the first body 13 apart from the at least one second body 14, fixed with respect to the first body 13 by means of an magnetic force; and moving the first body 13 along the linear direction X by a magnetic force so as to guide the thread 11 to apply it onto the substrate 12.

According to possible embodiments, the movement of the first body 13 can be obtained by means of a magnetic movement assembly 15 comprising a plurality of magnets 18, placed on the first body 13, and means 19 for generating a variable magnetic field, placed on the at least one second body 14.

In accordance with possible embodiments, the other magnetic force which moves the first body 13 along the linear direction X and the magnetic force which distances the first body 13 away from the at least one second body 14 can be generated by a single source, or rather can be generated by the magnetic movement assembly 15.

In accordance with possible embodiments, the method envisages generating electrical energy by electromagnetic induction, while the first body 13 decelerates.

This aspect makes it possible to generate electrical energy which can be used to supply parts of the guiding device 10 such as, for example, the spacer assembly 16, and/or other devices and/or apparatuses.

According to possible embodiments, the method may envisage setting a desired timetable defining the position of the first body 13 along the linear direction X in relation to time, and for moving the first body 13 according to the set timetable.

In accordance with possible embodiments, the method may envisage modulating the movement of the first body 13 in relation to the elasticity of the thread 11 and to the instantaneous position of the first body 13 along the linear direction X.

It is clear that modifications to the guiding device 10 of an apparatus for producing sanitary articles, and to the method for applying a thread 11 onto a substrate 12 intended for producing sanitary articles described up to now can be made and/or parts added, without thereby departing from the scope of the present invention.

It is also clear that, although the present invention has been described with reference to some specific examples, a person skilled in the art will certainly be able to produce many other equivalent forms of the guiding device 10 of an apparatus for producing sanitary articles, and of the method having the characteristics set forth in the claims and therefore all falling within the scope of protection defined therein.

In the following claims, the references in brackets have the sole object of facilitating the reading and should not be considered as limiting factors regarding the scope of protection underlying the specific claims.

The invention claimed is:

1. A guiding device of an apparatus for producing sanitary articles for applying at least one thread onto a substrate intended to produce said sanitary articles, comprising:
    a first body movable along a linear direction and configured to guide said thread,
    at least one second body at a fixed distance with respect to said first body,
    a spacer assembly configured to space said first body apart from said at least one second body by means of a magnetic force, wherein said spacer assembly comprises at least one air dispenser configured to dispense air so as to hinder access and/or deposition of contaminants between said first body and said at least one second body; and
    a magnetic movement assembly associated with said first body and with the at least one second body for moving said first body along said linear direction by means of another magnetic force.

2. The device as in claim 1, wherein said spacer assembly comprises a plurality of magnetic spacer elements each configured to generate a respective magnetic force in order to locally distance said first body from said at least one second body.

3. The device as in claim 2, wherein said plurality of magnetic spacer elements are placed at sides of said magnetic movement assembly.

4. The device as in claim 1, wherein said magnetic movement assembly comprises a plurality of magnets and means for generating a variable magnetic field in order to cooperate, in use, together for moving said first body along said linear direction by means of said another magnetic force.

5. The device as in claim 4, wherein said plurality of magnets is placed on said first body and said means for generating said variable magnetic field are placed on said at least one second body.

6. The device as in claim 1, further comprising at least two second bodies between which said first body is interposed.

7. The device as in claim 1, wherein a ratio between respective lengths along said linear direction of said first body and of said at least one second body is greater than 1.

* * * * *